United States Patent [19]

Wu et al.

[11] Patent Number: 6,100,447
[45] Date of Patent: Aug. 8, 2000

[54] METHOD OF BARLEY TRANSFORMATION

[75] Inventors: Liying Wu, Sacramento; Raymond L. Rodriguez, Davis, both of Calif.

[73] Assignee: Applied Phytologics, Inc., Sacramento, Calif.

[21] Appl. No.: 09/022,586

[22] Filed: Feb. 12, 1998

Related U.S. Application Data

[60] Provisional application No. 60/040,071, Feb. 12, 1997.

[51] Int. Cl.[7] .............................. A01H 1/00; A01H 5/00; A01H 4/100; C12N 15/82; C12N 15/87
[52] U.S. Cl. ........................ 800/278; 800/320; 435/468
[58] Field of Search ............................. 435/468; 800/278, 800/320

[56] References Cited

PUBLICATIONS

Potrykus. Ann. Review of Plant Physiol. 1991. vol. 42: 205–225.
Wan and Lemaux. Plant Physiology. 1994. vol. 104: 37–48.
Chan et al. The Journal of Biological Chemistry. 1994. vol.269: 17635–17641.
Chandler et al. Plant Molecular Biology. 1993. Nov. issue. vol. 23:737–747.

*Primary Examiner*—Lynette R. F. Smith
*Assistant Examiner*—Onsawa M-Foiz Zaphmont
*Attorney, Agent, or Firm*—Joanne R. Petithory; Peter J. Dehlinger

[57] ABSTRACT

A method for stably transforming barley from mature barley seeds as starting material is disclosed. The method involves germinating mature barley seeds until early shoot development occurs, exposing scutellar or embryo tissue cells on the embryo side of germinated seeds, and introducing foreign DNA into the cells. The cells are initially grown under conditions that allow expression of a selectable marker introduced with the foreign DNA, then on a callus-growth medium effective to suppress callus formation in the absence of the selectable marker. Successfully transformed calli can be cultured in suspension to obtain a desired foreign protein, or regenerated into plants, to obtain the foreign protein from the transformed plants, e.g., germinated seeds.

16 Claims, 3 Drawing Sheets

| STAGE | DAP | MAIN EVENTS |
|---|---|---|
| SYNCYTICIAL<br>I — IA / IB | 5 | ← Fertilization<br>← Syncytium formation<br>← Vacuolarization of cytoplasm |
| Cellularization<br>II — IIA / IIB | 6 | ← Cell wall initiation<br><br>← First cell plate formation |
| Differentiation<br>III — IIIA / IIIB | 8<br><br>14 | ← Cellularization complete<br>← Vacuolarization of aleurone meristem cells<br>← End of starchy-endosperm cell divisions |
| Maturation<br>IV | 21<br><br>40 | ← End of aleurone cell divisions<br><br>Accumulation of storage products |

Fig. 4

METHOD OF BARLEY TRANSFORMATION

This application claims the benefit of U.S. Provisional application Ser. No. 60/040,071 filed Feb. 12, 1997, which is incorporated herein by reference.

FIELD OF THE INVENTION

The present invention relates to a method for stably transforming barley, and to methods for obtaining foreign protein from stably transformed barley cells or plants.

BACKGROUND OF THE INVENTION

The ability to transform cereal grains through recombinant techniques has important applications in the agricultural industry—for example, in achieving hardier crops, insect resistance, or higher yields, or for expression in plants of exogenous proteins of interest.

Methods for stably transforming barley (*Hordeum vulgare*) have been demonstrated. These methods include, as example, the use of polyethylene glycol (PEG) or electroporation to facilitate DNA uptake by barley protoplasts, and particle bombardment of barley tissues, such as suspension cells, callus tissue and endosperm (Ritala, et al., *Plant Cell Reports* 12:435–440 (1993)). The challenge in these methods is to introduce foreign DNA into barley cells which are both totipotent and capable of stably integrating and expressing the foreign DNA.

Heretofore, stable transformation in barley has been achieved with cells (intact cells or protoplasts) obtained from early-stage embryos or surrounding scutellar tissue from early-growth seeds. Wan and Lemaux (*Plant Physiol.* 104:37–48 (1994)) reported successfully transforming barley plants using immature zygotic barley embryos as starting material. Chibbar et al. (WO 94/19930, published Sep. 15, 1994) disclose the regeneration of cereal plants, including barley, by introducing foreign into the scutellar tissue associated with immature zygotic embryos, typically obtained from early-development seeds 8–14 days post anthesis.

There is evidence that immature embryo cells are susceptible to stable transformation only during a short period in early embryogenesis (Wan, et al., supra). In order to prolong this period, and thus enhance the probability of successful transformation, it is standard practice currently to grow young barley plants under controlled temperature conditions, e.g., at 12–18° C. This approach, however, is relatively expensive and time-consuming in that special incubators must be employed, and the time required for plant growth and early seed development is typically 3–4 months.

Thus, although methods for transforming barley have been available heretofore, there remains a need for a relatively inexpensive, short-time period method for producing stably transformed barley plants and cells.

SUMMARY OF THE INVENTION

The present invention is directed to a method for stably transforming barley cells. The method includes the steps of germinating mature barley seeds until roots and shoots are evident, removing the roots and shoots from the germinating seeds to expose scutellar and/or embryo cells, and introducing the foreign nucleic acid into the exposed cells. The cells are cultured in callus-induction medium, and transformed cells are selected.

The procedure employs seeds which are easily stored and readily available at any time of year, and the entire procedure can be carried out in a matter of 4–6 weeks, including a 3–7 day germination period, a short period of recovery on non-selection medium, and a 2–3 week callus induction period.

The mature seeds may be in a dormant condition before germination, and are preferably prepared for germination by dehulling the mature seeds, and sterilizing the dehulled seeds. Endosperm tissue in the germinated seed may also be removed prior to introducing the foreign DNA. The germinating step is preferably carried out in a standard barley-callus induction medium.

Exemplary seeds are from Himalaya or Golden Promise varieties of barley.

In a preferred method, the foreign DNA introduced into the exposed cells includes a selectable marker gene. The cells are first cultured under conditions which allow expression of the selectable marker gene, then placed on callus induction medium effective to selectively suppress the growth of cells lacking the selectable marker gene. One exemplary selectable marker is phosphinothricin acetyltransferase, and the callus-induction medium contains phosphinothricin (PPT).

The foreign DNA may be introduced into the exposed cells, for example, tissue cells by particle bombardment, or by a combination of particle bombardment of the cells, to create sites susceptible to Agrobacterium infection, and coinfection by *Agrobacterium tumefaciens* and $T_i$ plasmid containing the foreign gene.

In one general embodiment, for use in producing a protein expressed by a gene in the foreign DNA, the transformed cells are cultured under cell culture conditions suitable for expression of the foreign gene. For example, the foreign gene may be under the control of the rice α-amylase RAmy3D or RAmy3E promoter, with the cells being cultured under conditions of sugar depletion in the culture medium.

In another general embodiment for protein production in transformed plant tissue, the transformed callus is used to regenerate a barley plant, and protein is obtained from mature seeds after seed germination. The gene encoding the foreign protein is under the control of an α-amylase promoter which is inducible during seed germination.

These and other objects and features of the invention will become more fully apparent when the following detailed description of the invention is considered with the accompanying drawings.

BRIEF DESCRIPTION OF THE DRAWINGS

FIG. 4 shows the stages of barley seed development.

DETAILED DESCRIPTION OF THE INVENTION

I. Definitions

The terms below have the following meaning, unless indicated otherwise in the specification.

"Barley seed(s)" refers to seed(s) from any variety or cultivar of barley (*Hordeum vulgare*), including but not limited to, Golden Promise and Himalaya.

"Mature barley seed" refers to a barley seed with completed seed development, preferably in a dormant state.

"Scutellum" or "scutellar tissue" refers to the tissue of the barley seed that lies between the embryo and the endosperm, including a layer of scutellar epithelial cells.

"Seed germination" refers to the process of resumption of embryo development in the seed, and breakdown of endosperm food reserves to fuel embryo growth.

"Callus" or "callus tissue" refers to undifferentiated plant cells, e.g., derived from transformed scuteller tissue cells after DNA bombardment.

"Foreign", as applied to DNA or a gene or a protein, refers to DNA or a gene or protein that not endogenous to barley plants.

"Callus induction media" as used herein refers to any culture media which induces the growth of callus from the scutellar or embryo cells derived from mature barley seeds.

"Stably transformed" as used herein refers to a barley cell or plant that has foreign nucleic acid integrated into its genome which is maintained from one generation to another.

"Cell culture" as used herein refers to a culture of plant cells, typically callus cells or cell clumps, cultured in a suitable growth medium.

"Gene product" refers to a polypeptide or protein encoded by a nucleic acid sequence.

"Media effective to suppress the growth of cells lacking the selectable marker gene" refers to media that restricts the growth of non-transformed barley cells while allowing for the growth of transformed barley cells. For example, the bar gene, which codes for phosphinothricin acetyltransferase, confers resistance to phosphinothricin (PPT) the active ingredient in commercially available herbicides. Co-transformation of barley cells with the bar nucleic acid and a desired foreign nucleic acid would render the transformed cells resistant to PPT, whereas non-transformed cells would die in the presence of PPT.

"Selectable marker gene" refers to nucleic acid encoding a protein which confers resistance to an herbicide, antibiotic or other agent. As will be understood by those of skill in the art, proteins having additional functions may also be used as selectable markers.

II. Transformation of Mature Barley Seeds

The procedure starts with mature, preferably dormant barley seeds. These are available from any reliable seed source or seed supplier. Exemplary barley strains for use in the invention are Himalaya and Golden Promise, although other barley strains are suitable.

A. Preparing Seeds for Transformation

Figure 1:
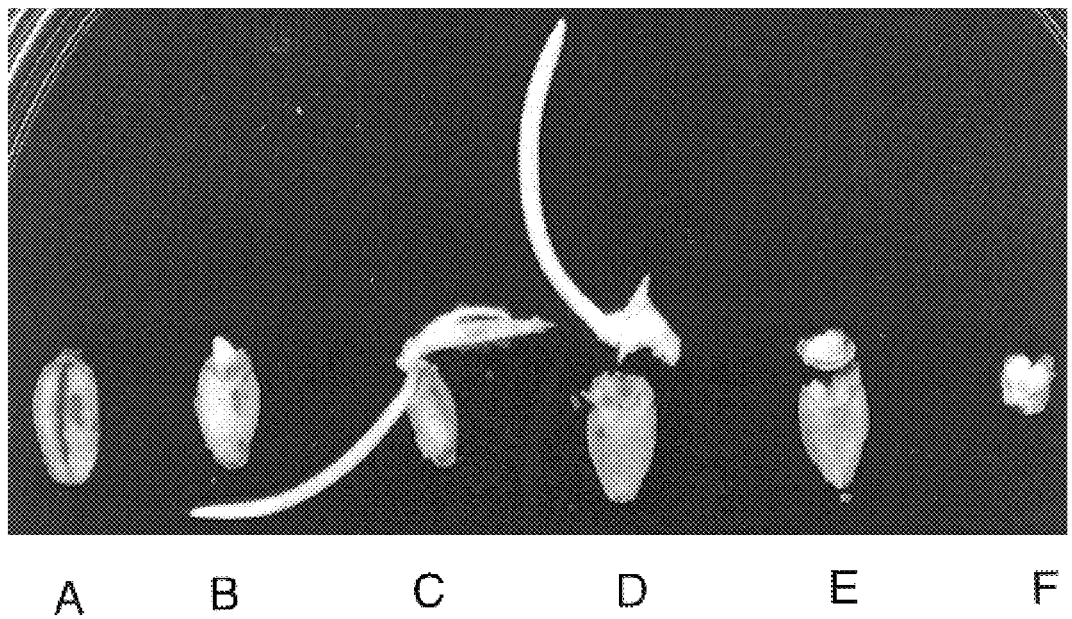
FIGS. 1A–1F are computer-generated reproductions of photographs of a mature barley seed seen from dorsal and ventral sides (1A and 1B), during germination (1C), with the embryo dissected away (1D), with the scutellum exposed (1E), and with the endosperm dissected away (1F), illustrating seed preparation steps in accordance with one embodiment of the invention.

Procedures for preparing mature-seed scutellar tissue for transformation are detailed in the example below. Briefly, mature, dormant seeds are dehulled and sterilized (FIGS. 1A and 1B), then placed on a barley callus-induction medium, e.g., the BCI medium described below, effective to promote seed germination. Germination, e.g., at 25° C., is continued until seed shoots are about 2 cm in length, typically over a germination period of 3–7 days, as illustrated in FIG. 1C.

Method 1: Scutellar bowl. After germination, roots and shoots are removed (FIG. 1D), exposing the scutellum. The endosperm of the germinated seeds may also be removed (FIG. 1E), to yield intact scutellum, which is bowl-shaped and about 2–3 mm in diameter. The scutellar tissue is placed bowl-shape up on a phytagel plate containing a standard barley callus induction medium, e.g., the BCI-0 medium described below, for about 4–8 hours (Gamborg, et al. (Eds.), *PLANT CELL TISSUE AND ORGAN CULTURE*, Springer-Verlag (1995)).

Method 2: longitudinal half embryos. In this method, a mature barley seed is cut along its longitudinal bilateral axis, to expose scutellar and longitudinal embryo tissue, as diagramed in FIG. 2. The figure shows a barley seed 10, and scutellar cells 12 and embryo 14 exposed by a longitudinal cut. In addition, the major portion of the endosperm is cut away, e.g., with a cut along line 16 in the figure.

Method 3: longitudinal half embryos. In this method, a mature barley seed is cut along an axial cutting plane, such as the plane indicated by cut line 18 in FIG. 2. The cut line is preferably below the root and shoot tissue in the embryo, as seen, and exposes scutellar cells 12 and axial embryo tissue below the cut line in the figure. As in Method 2, the major portion of the endosperm is cut away, e.g., with a cut along line 16 in the figure.

B. Preparation of Foreign DNA

Expression vectors for use in the present invention are designed for operation in plants, with companion sequences upstream and downstream from the desired foreign nucleic acid, as detailed, for example, in PCT patent application Ser. No. WO 95/14099, published May 26, 1995, which is incorporated herein by reference.

The companion sequences will be of plasmid or viral origin and will provide the necessary characteristics to the vector to permit the vector to move nucleic acid from bacteria to the barley tissue. Sequences suitable for permitting integration of a foreign sequence into the plant genome are recommended and might include transposon sequences as well as Ti sequences which permit random insertion of a foreign expression vector into the barley genome.

As will be understood by those of skill in the art, in addition to foreign nucleic acid sequence, the expression vector may include a promoter region, plant 5' untranslated sequences, initiating codon if the foreign nucleic acid does not have one, and transcriptional and translational termination sequences (Sambrook, et al., *MOLECULAR CLONING-A LABORATORY MANUAL*, Cold Spring Harbor Laboratory, Cold Spring Harbor, N.Y. (1989)). The expression vector may also contain unique restriction enzyme sites at the 5' and 3' ends to allow for ease of genetic engineering.

The expression vector may also include a signal sequence that allows the foreign protein to be secreted from the cells in which it is produced allowing for the isolation and purification of the foreign protein. Examples of signal sequences from wheat, barley and rice that facilitate secretion of foreign proteins into the endosperm of the seeds are given in Rodriguez (WO 95/14099, supra). Those of skill in the art will be able to identify additional useful sequences, for example by applying standard nucleic acid hybridization conditions, including PCR technology, and probing DNA libraries derived from other monocots.

In one embodiment of the invention, particularly for use in protein expression in cell culture, the expression construct includes a transcription regulatory region, i.e., a promoter whose transcription is specifically regulated by the presence or absence of a small molecule, e.g., the rice α-amylase RAmy3D or RAmy3E promoters (Huang, N, et al., *Nuc. Acids Res.* 18(23):7007 (1990)), and the sucrose synthase and sucrose-6-phosphate synthetase (SPS) promoters from rice and barley (Huang, supra, and references cited therein), all of which are upregulated in plant cell culture by sugar depletion.

In another embodiment of the present invention, particularly for use in protein expression in germinating plant seeds, the promoter is hormonally regulated by molecules such as the phytohormones gibberellic acid or abscisic acid, e.g., the rice α-amylase RAmy1A promoter, or barley α-amylase HV18 promoter.

One exemplary foreign DNA vector contains the RAmy1A α-amylase promoter (Huang, N. et al., *Plant Mol Biol.* 14:655 (1990); Itoh, K. et al., Plant Physiol. 107:25 (1995)) to control expression of the gusA gene which encodes the enzyme beta-glucuronidase (GUS). Cells successfully transformed with the enzyme produce a blue chromophore in tissues expressing the gene when exposed to an appropriate substrate. It will be appreciated that the gusA gene is representative of the coding sequence for any polypeptide or protein to be produced in the transformed cells, such as the foreign proteins set out in above-cited PCT application Ser. No. WO 95/14099.

The plants are preferably also transformed with a selectable marker gene which allows selection of transformed cells based on growth in a selected medium. The selectable marker gene may be carried on the same construct as the foreign gene to the expressed, or in a separate construct used to co-transform scutellar cells. In the example below, the selectable marker is the gene for phosphinothricin acetyltransferase (bar gene), whose expression permits cell growth on a medium containing the herbicide phosphinothricin (PPT). The selectable marker is contained on a separate plasmid, and is under the control of the maize ubiquitin promoter (Christensen, et al., Transgenic Res. 5(3):213 (1992); Toki, et al., *Plant Physiol.* 100(3):1503 (1992)).

C. Introducing Foreign DNA

A variety of methods for introducing DNA into plant cells or protoplasts have been reported in the art (Potrykus, *Annu. Rev. Plant Physio. Plant Mol. Bio.* 42:205–225 (1991)). The methods include, but are not limited to, gene transfer methods which rely on electroporation (Fromm, et al. *Proc. Natl. Acad. Sci.* USA 82:5824 (1985)); protoplast fusion methods which transfer DNA through the plasma membrane (Zhang et al., *Theor. Appl. Genet.* 76:835–840 (1988)); Agrobacterium-mediated transformation (Chan et al., *Plant Mol. Biol.* 22:491–246 (1993)); and direct particle bombardment wherein cells or tissues are bombarded with tungsten or gold particles that are coated with a desired nucleic acid (Klein et al., *Nature (London)* 327:70–73 (1987)).

A preferred transformation method of the present invention is the particle bombardment method described, for example, in Wan et al., (1994; supra). In this method, foreign-DNA plasmid is adsorbed to gold particles (1.0 μm particles, DuPont, Wilmington, Del.). When two plasmid DNA constructs are used to transform plant tissue, a mixture of the two plasmids may be adsorbed to the gold particles for co-injection, as described in the example below.

The invention contemplates the use of the particle bombardment method alone or in combination with other methods, such as the Agrobacterium-mediated transformation method. For example, the particle bombardment method may be used first to prepare barley scutellum that is susceptible to infection followed by infection by Agrobacterium (Bidney, et al., *Plant Mol. Biol.*, 18:301 (1991)). Furthermore, mature barley scutellar tissue may be transformed with a desired nucleic acid alone or in combination with other nucleic acids such as a selectable marker gene. A general review of suitable marker genes for barley is found in Wilmink and Dons, *Plant Mol. Biol. Reptr.* 11(2):165–185 (1993)).

D. Selecting Transformed Calli

After introducing the foreign DNA, e.g., by particle bombardment, the scutellum is allowed to recover by continued culturing on the same callus-induction medium (recovery phase). The culturing on permissive medium, (e.g., BCI-O, Example 1 below) is carried out for a period, e.g., 1–3 days, sufficient to allow expression of the selectable marker gene to levels adequate for cell selection on a selection medium.

The scutellum is then placed bowl down, i.e., with its concave surface facing the medium, either intact or in 3–4 pieces, on a callus-induction medium that is permissive for callus-cell growth only in cells expressing the selectable marker. In the example below, where the selectable marker gene is the bar gene, the growth medium contains 5 mg/L of the herbicide phosphinothricin (PPT) (Bialaphos) (BCI-5B medium, Example 1).

Callus induction is allowed to proceed at 25° C. for 2–3 weeks, until healthy calli are obtained. These calli can be distinguished from non-transformed calli based on their larger, healthier appearance.

To confirm that the callus identified as transformed are also transformed with the foreign gene of interest, a portion of the healthy calli may also be processed or cultured under conditions which allow expression of the foreign protein of interest to be detected. For example, where the foreign gene is under the control of a promoter that is up-regulatable in a selected culture medium, the callus cells may be cultured in that medium, and the medium or cells then examined for expression of the protein.

In the example below, where the foreign gene is the gusA gene, a portion of the callus is placed in a culture medium containing an indole β-glucuronide substrate (X-gluc). The appearance of blue dots in the tissue indicate expression of the foreign gene.

III. Production of Foreign Proteins

This section briefly describes preferred methods for producing foreign proteins in barley cells transformed in accordance with the invention. The methods generally follow known plant-cell expression methods, such as detailed in the above-cited PCT application Ser. No. WO 95/14099.

A. Expression in Cell Culture

Transgenic cells, e.g., callus cells, are broken into small clumps of typically 1–20 or more cells, and suspended in a suitable cell culture medium. The cells are preferably cultured under conditions that favor plant cell growth, until the cells reach a desired cell density, then under conditions that favor expression of the gene under the control of the given promoter.

In one embodiment of the invention, where the promoter is the rice α-amylase RAmy3D or RAmy3E promoter, the cells are initially placed in culture medium containing 3 percent sucrose, as described in the example below. Over a culture period of 5–10 days, the amount sucrose in the medium declines from 3 to 0 percent. The depletion of sucrose in the medium up-regulates the 3D or 3E promoter, with the concomitant increase in expression levels of the foreign protein.

Foreign protein, if expressed and secreted in culture, may be isolated from the culture medium by standard methods.

B. Foreign Protein Production in Germinating Seeds

Plant regeneration from transformed callus cells follows standard methods, e.g., as outlined by Evans, et al., *HANDBOOK OF PLANT CELL CULTURES*, Vol. 1: (MacMillan Publishing Co. New York, 1983); Vasil I. R. (Ed.), *CELL CULTURE AND SOMATIC CELL GENETICS OF PLANTS*, Acad. Press, Orlando, Vol. I, 1984, and Vol. III, 1986; and Wan, supra.

The mature plants, grown from the transformed plant cells, are selfed and non-segregating, homozygous transgenic plants are identified. The inbred plant produces seed containing the chimeric gene of the present invention. These seeds are then malted by standard methods to produce the foreign protein of interest, where the foreign protein is preferably under the control of a promoter which is upregulated during seed germination. Suitable seed malting procedures and methods for obtaining proteins from barley malt are discussed in above-cited WO 95/14099.

Figure 3:
FIG. 3 is a computer-generated reproduction of a photograph showing GUS expression in transformed mature barley scutellar tissue, as evidenced by the presence of dark dots (arrows)

Various objects and advantages of the present invention will now be considered with reference to FIG. 3, which illustrates characteristic stages of embryogenesis and seed development in plants, expressed in days after flowering (the total period for barley is 2–3 months). As seen, the developmental stages include an early embryogenesis stage, a middle stage of seed protein and lipid accumulation, during which the seed dry weight increases dramatically and reaches its fully mature seed weight, and a dormancy stage during which RNA and protein synthesis shut down, and the seed loses water.

To transform barley during early embryogenesis—the most common method heretofore—it is necessary to (i) grow plants under controlled conditions up to and into the embryogenesis stage of seed development, (ii) transform the early-stage embryo tissue, and (iii) select transformed callus tissue. As noted above, the first step requires several months plant growth under controlled temperature conditions.

In the present invention, by contrast, embryo and scutellar tissue cells are prepared for transformation by germinating mature seeds (seeds which have reached or passed the dormancy stage) for a period of a few days. The seeds may be obtained from any of a number of commercial seeds sources, and may be readily stored over a period of several months or more, until ready for use. Thus, the method significantly reduces cost and time of transformation, and allows greater flexibility in terms of seed source and timing of transformation protocols.

From the foregoing, it will be appreciated how various objects and features of the invention are met. As noted above, prior-art methods have focused on transforming cells from early-stage embryos and surrounding scutellar tissue. With reference to FIG. 4, this early stage would correspond to the completion of cellularization to the end of starch endosperm cell divisions. As noted above, special growth conditions are generally employed to extend this period, to optimize transformation efficiency.

By contrast the present invention allows for transformation of embryo and/or scutellar cells in mature barley seeds, i. e., after the maturation step in FIG. 4 and further seed-dehydration. Mature seeds are readily stored and obtained, and are easily prepared for cell transformation simply by subjecting the seeds to a short germination period (3–7 days), followed by a short recovery period on non-selection medium, and one or more callus induction steps, each 2–3 weeks. As a result, transformation for cell culture can be carried out in a total of 4–6 weeks, using seeds that are readily obtainable at any time of year and easily stored until needed.

The following examples of the transformation of barley cells from mature seeds is intended to illustrate, but in no way limit, the invention.

The following media were used in the example:

TABLE 1

| | BCI | BCI-O | BCI-5B | FHG-3B | RM-5B |
|---|---|---|---|---|---|
| Macro elements (mg/l) | | | | | |
| KNO$_3$ | 1900 | 1900 | 1900 | 1900 | 1900 |
| NH$_4$NO$_3$ | 1650 | 1650 | 1650 | 165 | 1650 |
| CaCl$_2$ | 332.2 | 332.2 | 332.2 | 332.2 | 332.2 |
| MgSO$_4$ | 180.7 | 180.7 | 180.7 | 180.7 | 180.7 |
| KH$_2$PO$_4$ | 170 | 170 | 170 | 170 | 170 |
| Na$_2$-EDTA | 37.26 | 37.26 | 37.26 | 33.5 | 37.26 |
| FeSO$_4$ 7H$_2$O | | | | 27.8 | |
| Micro elements (mg/l) | | | | | |
| MnSO$_4$ H$_2$O | 16.9 | 16.9 | 16.9 | 16.9 | 16.9 |
| ZnSO$_4$ 7H$_2$O | 8.6 | 8.6 | 8.6 | 8.6 | 8.6 |
| H$_3$BO$_3$ | 6.2 | 6.2 | 6.2 | 6.2 | 6.2 |
| KI | 0.83 | 0.83 | 0.83 | 0.83 | 0.83 |
| CoCl$_2$ 6H$_2$O | 0.025 | 0.025 | 0.025 | 0.025 | 0.025 |
| CuSO$_4$ 5H$_2$O | 0.025 | 0.025 | 0.025 | 0.025 | 0.025 |
| Na$_2$MoO$_4$ 2H$_2$O | | | | 0.25 | |
| Vitamins (mg/l) | | | | | |
| myo-Inositol | 350 | 350 | 350 | 100 | 350 |
| Thiamine-HCl | 1.1 | 1.1 | 1.1 | 0.4 | 1.1 |
| Nicotinic Acid (Free acid) | 0.5 | 0.5 | 0.5 | | 0.5 |
| Pyridoxine-HCl | 0.5 | 0.5 | 0.5 | | 0.5 |
| Amino acids (mg/l) | | | | | |
| Casein hydrolysate | 1000 | 1000 | 1000 | | 1000 |
| L-Proline | 690 | 690 | 690 | | 690 |
| L-Glutamine | | | | 730 | |
| Glycine (Free base) | 2 | 2 | 2 | | 2 |
| Sugars (g/l) | | | | | |
| Maltose | 30 | 30 | 30 | 30 | 30 |
| Mannitol | | 37.2 | | | |
| Sorbitol | | 37.2 | | | |
| Growth regulators (mg/l) | | | | | |
| 6-Benzylaminopurine (BA) | | | | 1 | |
| Dicamba | 2.5 | 2.5 | 2.5 | | |
| Selectives (mg/l) | | | | | |
| Bialaphos | | | 5 | 3 | 5 |
| Agarose (g/l) | | | | | |
| Phytagel | 3 | 3 | 3 | 3 | 3 |
| pH | 5.8 | 5.8 | 5.8 | 5.8 | 5.8 |

EXAMPLE 1

Transformation Method Applied to Scutellar Seed Bowl

1. Seed Sterilization

Mature, dormant barley seeds of the Golden Promise or Himalaya variety were selected for the transformation procedure. Clean mold-free seeds were selected, and the selected seeds were dehulled with forceps.

The following steps were performed in a sterile area. The dehulled seeds were soaked in 70% ethanol for one minute, and rinsed with doubly deionized sterile water (ddH$_2$O). The dehulled seeds were placed in a flask containing 50% bleach and a sponge plug was used as a lid. The flask was placed in a vacuum desiccator and the seeds were stirred under vacuum for 20 minutes. After stirring, the seeds were allowed to sit without stirring or vacuum for 10 minutes. The seeds were rinsed with sterile ddH$_2$O and washed three times for 5 minutes each time.

2. Seed Germination

The sterile seeds were placed onto Barley Calli Induction medium (BCI) and incubated approximately 3–7 days at 25° C., until the shoots were about 2 cm in length.

3. Scutellum Preparation and Pretreatment

The intact scutellum was isolated from the embryo by the steps illustrated in FIGS. 1A–1F. As shown in FIG. 1D, the roots and shoots were carefully removed from the germinating seeds with forceps. Next (FIG. 1E), the endosperm was carefully removed from the geminating seeds. The isolated scutellum appeared bowl-shaped, 2–3 mm in diameter, white, and firm. An intact scutellum may be used for the transformation procedure, however scutellar tissue that is torn into several pieces during the dissection may also be used for the transformation procedure. It is important to keep the scutellum tissue moist during the preparation.

Isolated scutellum is placed bowl-shape up onto BCI-O (Barley Calli Induction-Osmotic) medium for 5 hours in preparation for transformation.

4. Particle Washing and Coating

Gold particles were coated with a DNA vector encoding the β-glucuronidase (GUS) gene, under the control of the rice amylase promoter RAmy3D, as described above. Particles for use in the transformation procedure were prepared as follows. Six mg of 1.0 μm gold particle and 6 mg 1.6 μm gold particle were placed separately into two sterile 1.5 ml centrifuge tubes. The tubes were vortexed for 1–2 minutes with 100 μl of 100% ethanol per tube. The tubes were centrifuged for 10 seconds and the resultant supernatant was discarded. The tubes were vortexed for 1–2 minutes with 100 μl of sterile $ddH_2O$, centrifuged for 10 seconds and the supernatants discarded. The vortexing and centrifugation steps with $ddH_2O$ were repeated two times. The gold particles were resuspended in 100 μl of sterile dd $H_2O$, then the two tubes were mixed together.

Under sterile conditions, 50 μl of washed gold particles were placed in a siliconized, sterilized centrifuge tube. As shown below, the two plasmids pBI221 (containing nucleic acid encoding GUS; Clontech, Palo Alto, Calif.) and pAHC20 (containing nucleic acid encoding the bar gene product (Christensen, supra, and Toki, supra) were mixed by a molar ratio of target gene to selectable marker gene 1–6:1. 5–20 μg of DNA was added to each tube and 20 μl of 0.1 M spermidine free base was added while vortexing. Slowly, in a dropwise fashion while vortexing, 50 μl of 2.5 M $CaCl_2$ was added. The solution was allowed to stand at room temperature for 10 minutes. The solution was centrifuged for 10 seconds and the supernatant was discarded. The particles were resuspended in 60 μl of 100% ethanol by gently flicking the end of the tube. 10 μl of the particle was loaded onto one microcarrier as evenly as possible.

Experiment 1

In experiment 1, the barley cultivar was Golden Promise and the bombardment was with pBI221 (5.7 kb) at a concentration of 1 μg/μl and pAHC20 (5.2 kb) at a concentration of 1 μg/μl. The ratio of the two plasmids was 6:1 and the DNA amount was 3.3 μg/plate. The ratio of the particles was 1:1 (1.0 μM and 1.6 μM) and the particle amount was 1 mg/plate. Three plates of isolated mature scutellum were used from germinated seeds.

Experiment 2

In experiment 2, the barley cultivar was Himalaya and the bombardment was with pBI221 (5.7 kb) at a concentration of 1 μg/μl and pAHC20 (5.2 kb) at a concentration of 1 μg/μl. The ratio of the two plasmids was 6:1 and the DNA amount was 3.3 μg/plate. The ratio of the particles was 1:1 (1.0 μM and 1.6 μM) and the particle amount was 1 mg/plate. Three plates of isolated mature scutellum were used from germinated seeds.

Experiment 3

In experiment 3, the barley cultivar was Golden Promise and the bombardment was with pBI221 (5.7 kb) at a concentration of 1 μg/μl and pAHC20 (5.2 kb) at a concentration of 1 μg/μl. The ratio of the two plasmids was 1:1 and the DNA amount was 6 μg/plate. The ratio of the particles was 1:1 (1.0 μM and 1.6 μM) and the particle amount was 1 mg/plate. 49 mature scutellum were used from germinated seeds. There were two plates of experimental transformations.

5. Particle Bombardment

The particles prepared by the method above were bombarded onto the previously prepared mature scutellar tissue. The particles were bombarded under a vacuum of 28 in. Hg with a rupture pressure of 1100 psi and a target distance of 8 cm. The plates containing the prepared scutellar tissue were bombarded twice per plate with a 180° rotation between bombardments. The bombarded scutellar tissue was allowed to recover by keeping the bombarded scutellar on the same BCI-O medium at 25° C. for an additional 48 hours.

6. Calli Induction

Each scutellum was torn into 4 pieces or alternatively the scutellum was left in its original size and placed bowl-shaped down onto BCI-5B medium (Barley Calli Induction with the addition of 5 mg Bialaphos; Meiji Seika Kaisha, Ltd, Tokyo, Japan) and incubated at 25° C. for 2–3 weeks.

7. Expression

20% of the total bombarded scutellum was analyzed for GUS expression. The GUS assays were performed 48 hours after bombardment by soaking the scutellum in a solution of 1.0 mM X-gluc (Gold Biotechnology, Inc. 8620 Pennell Drive St., Louis, Mo.) for 24 hours at 37° C., where blue dots represent transformed cells.

Results

As illustrated by FIG. 3, scutellar tissue transformed by pBI221 and pAHC20 expressed GUS (the dark spots representing transformed cells). In Experiment 1, there were 3 blue dots per 15 scutellum; in Experiment 2, there were 7 dots per 10 scutellum; in Experiment 3, on one plate there were 3 blue dots per 7 scutellum and on the second plate there were 0 blue dots per 3 scutellum.

EXAMPLE 2

Transformation Method Applied to

Longitudinally Dissected Barley Seed

Figure 2:
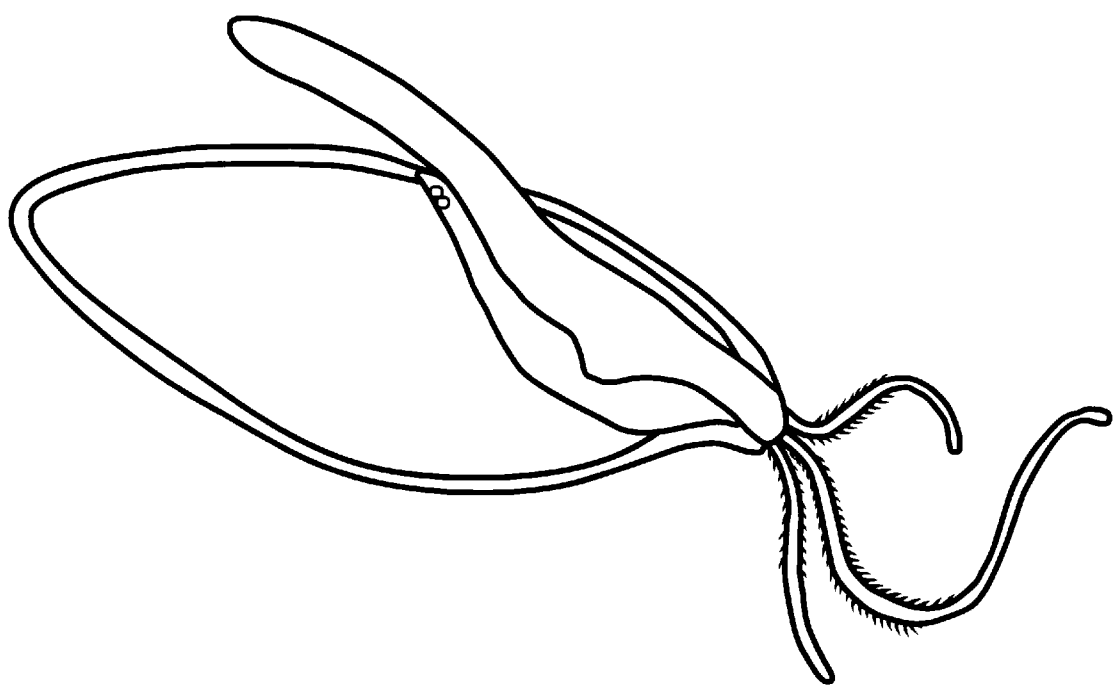
FIG. 2 is a longitudinal cutaway view of a barley seed, with endosperm tissue cut away, illustrating the exposed embryo and scutellar barley-seed cells in another embodiment of the invention, and the axial cut line in a third embodiment of the invention.

Mature, dormant barley seeds were sterilized and germinated as in Example 1. The seeds were cut longitudinally, i.e., along the bilateral axis of the seed, and a major portion of the endosperm was removed by cutting, yielding embryo and scutellar cells exposed as illustrated in FIG. 2. The seed portions were placed scutellum side (cut surface) up on BCI-O for 5 hours in preparation for transformation.

The seed portion was bombarded with gold particles carrying plasmids (1:1 ratio) having the GUS and selectable marker genes, as in Example 1, by bombarding the scutellar and embryo side of the seeds. The bombarded tissue was allowed to recover by keeping the bombarded scutellar on the same BCI-O medium at 25° C. for an additional 48 hours. Thereafter, the seed portions were placed cut surface down onto BCI-5B medium and incubated at 25° C. for 14 days, then transferred to onto fresh BCI-5B media every two weeks.

Results 73 half embryos were induced for callus. Of these, 23 viable calli were formed after 20 days on BCI-5B media. GUS assays performed two days after bombardment showed: 25 half embryos yielded 135 blue dots; one half embryo yielded 28 blue dots, and another, 31 blue dots.

EXAMPLE 3

Transformation Method Applied to Longitudinally Dissected Barley Seed

Mature, dormant barley seeds (Harrington and Golden Promise) were sterilized and germinated as in Example 1. The seeds were cut axially, i.e., along the axial (asymmetric) plane indicated by the cutting line in FIG. 2, slicing away root and shoot tissue to expose scutellum and embryo axis tissue. The seed portions were placed scutellum side (cut surface) up on BCI-O for 5 hours in preparation for transformation.

The seed portion was bombarded with gold particles carrying plasmids (1:1 ratio) having the GUS and selectable marker genes, as in Example 1, by bombarding the scutellar and embryo side of the seeds. The bombarded tissue was allowed to recover by keeping the bombarded scutellar on the same BCI-O medium at 25° C. for an additional 48 hours. Thereafter, the seed portions were placed cut surface down onto BCI-5B medium and incubated at 25° C. for 14 days, then transferred to onto fresh BCI-5B media every two weeks.

Results

59 Harrington scutellum embryos out of 94 were induced to calli after culturing on BCI-5B medium for 5 days. 77 Golden Promise scutellum-embryos out of 84 were induced to calli under the same conditions.

GUS assays performed on the Harrington seeds two days after bombardment showed 11 scutellum-embryos with 19 blue dots, and for Golden Promise, 32 scutellum-embryos yielded 8 blue dots and another, yielded 7 blue dots.

Although the foregoing invention has been described in some detail by way of specific methods, examples and constructs, it will be appreciated that various changes and modification may be made without departing from the invention.

It is claimed:

1. A method of transforming barley cells with foreign nucleic acid comprising the steps of:
    (a) germinating mature barley seeds until roots and shoots are evident, wherein said seeds are in a dormant stage prior to germination;
    (b) exposing either scutellar or embryo cells, or both, in the germinated seeds,
    (c) contacting the exposed cells on callus induction medium for a period of several hours to a few days,
    (d) introducing the foreign nucleic acid into the exposed cells;
    (e) culturing the cells in callus-induction medium; and
    (f) selecting transformed callus cells.

2. The method of claim 1, wherein said mature barley seeds are in a dormant stage prior to germinating the seeds.

3. The method of claim 1, which further includes, at the time of said exposing, removing endosperm tissue from the seed.

4. The method of claim 1, wherein said exposing includes removing the entire embryo to expose a bowl-shaped layer of scutellum cells.

5. The method of claim 1, wherein said exposing includes bisecting the seeds longitudinally, through the bilateral embryo axis.

6. The method of claim 1, wherein said exposing includes cutting the seed along the embryo long axis, to expose embryo axis tissue.

7. The method of claim 1, wherein said germinating step is carried out in a barley-callus induction medium.

8. The method of claim 1, wherein the foreign nucleic acid introduced into the exposed cells includes a selectable marker gene, and said culturing step includes culturing the cells under conditions allowing expression of the selectable marker gene, then placing the cultured cells on callus induction medium effective to selectively suppress the growth of cells lacking the selectable marker gene.

9. The method of claim 8, wherein said selectable marker is phosphinothricin acetyltransferase, and the callus-induction medium contains phosphinothricin (PPT).

10. The method of claim 1, wherein the foreign DNA is introduced into the exposed cells by particle bombardment.

11. The method of claim 1, wherein the foreign DNA is introduced into the exposed cells by a combination of particle bombardment of the cells, to create sites susceptible to Agrobacterium infection, and coinfection by *Agrobacterium tumefaciens* and $T_i$ plasmid containing the foreign gene.

12. The method of claim 1, wherein the mature barley seeds are obtained from Himalayan or Golden Promise varieties of barley.

13. The method of claim 1, wherein the foreign nucleic acid is expressed in transformed cells to produce a protein.

14. The method of claim 13, wherein said foreign DNA includes the coding region of the protein to be expressed, under the control of the rice α-amylase promoters RAmy3D or RAmy3E, and said cells are cultured in cell culture under conditions of sugar depletion in the culture medium.

15. The method of claim 1, wherein the foreign nucleic acid is expressed in transformed callus cells to produce a protein, which further comprises regenerating a transgenic barley plant from transformed callus cells.

16. The method of claim 1, which further comprises growing the transformed callus under conditions effective to regenerate a barley plant, obtaining seeds from the barley plants, growing plants from the said seeds and selecting those plants that express the foreign nucleic acid.

* * * * *